United States Patent [19]

Varma

[11] Patent Number: 5,622,826
[45] Date of Patent: Apr. 22, 1997

[54] METHOD FOR IMMOBILIZATION OF MOLECULES ON PLATINUM SOLID SUPPORT SURFACES

[75] Inventor: Rajender S. Varma, The Woodlands, Tex.

[73] Assignee: Houston Advanced Research Center, The Woodlands, Tex.

[21] Appl. No.: 362,264

[22] Filed: Dec. 22, 1994

[51] Int. Cl.$^6$ .................................................. C12Q 1/68
[52] U.S. Cl. ............................ 435/6; 536/24.3; 536/25.3
[58] Field of Search .............................. 435/6; 536/24.3, 536/25.3

[56] References Cited

U.S. PATENT DOCUMENTS

| | | | |
|---|---|---|---|
| 4,098,645 | 7/1978 | Hartdegen et al. | 195/68 |
| 4,293,310 | 10/1981 | Weber | 23/230 B |
| 4,414,323 | 11/1983 | Masuda | 435/7 |
| 4,414,325 | 11/1983 | Masuda et al. | 435/7 |
| 5,001,051 | 3/1991 | Miller et al. | 435/6 |
| 5,143,854 | 9/1992 | Pirrung et al. | 436/518 |
| 5,153,166 | 10/1992 | Jain et al. | 502/402 |
| 5,241,012 | 8/1993 | Clark | 525/333.6 |
| 5,314,830 | 5/1994 | Anderson et al. | 436/524 |

OTHER PUBLICATIONS

Akashi, Mitsuru et al., "Immobilization of Human Thrombomodulin on Glass Beads and Its Anticoagulant Activity," *Bioconjugate Chem.* 3:363–365 (1992).

Beattie, Kenneth et al., "Genosensor Technology," *Clinical Chemistry* 39:719–722 (1993).

Bhatia, Suresh K. et al., "Immobilization of acetylcholinesterase on solid surfaces: chemistry and activity studies," *Sensors and Activators B.* 3:311–317 (1991).

Bhatia, Suresh K. et al., "Use of Thiol-Terminal Silanes and Heterobifunctional Crosslinkers for Immobilization of Antibodies on Silica Surfaces," *Analytical Biochemistry* 178:408–413 (1989).

Bhatia, Suresh K. et al., "Fabrication of Surfaces Resistant to Protein Adsorption and Application to Two-Dimensional Protein Patterning," *Analytical Biochemistry* 208:197–205 (1993).

Cormia, Robert, "Engineering Polymer Surfaces for Biological Compatibility," *R&D Magazine* 51–52 (Jun. 1993).

Drmanac, R. et al., "DNA Sequence Determination by Hybridization: A Strategy for Efficient Large-Scale Sequencing," *Science* 260:1649–1652 (1993).

Duevel, Robert V. et al., "Amide and Ester Surface Attachment Reactions for Alkanethiol Monolayers at Gold Surfaces As Studied by Polarization Modulation Fourier Transform Infrared Spectroscopy," *Anal. Chem.* 64:337–342 (1992).

Fahy, Eoin et al., "Design and synthesis of polyacrylamide-based oligonucleotide supports for use in nucleic acid diagnostics," *Nucleic Acids Research* 21:1819–1826 (1993).

Lamture, Jagannath B. et al., "Direct detection of nucleic acid hybridization on the surface of a charge coupled device," *Nucleic Acids Research* 22:2121–2125 (1994).

Maskos, Uwe et al., "Oligonucleotide hybridisations on glass supports: a novel linker for oligonucleotide synthesis and hybridisation properties of oligonucleotides synthesised in situ," *Nucleic Acids Research* 20:1679–1684 (1992).

Matson, Robert S. et al., "Biopolymer Synthesis on polypropylene Supports," *Analytical Biochemistry* 217:306–310 (1994).

(List continued on next page.)

*Primary Examiner*—Scott W. Houtteman
*Attorney, Agent, or Firm*—Michael A. Sanzo; Vinson & Elkins

[57] ABSTRACT

The present invention is directed to methods for immobilizing molecules on surfaces of platinum. Devices having surfaces modified by such methods are also claimed. The method uses an isocyanate or isothiocyanate molecule which is reacted with the platinum to produce immobilized reactive moieties. These moieties are reacted with the molecule to be immobilized.

10 Claims, 11 Drawing Sheets

OTHER PUBLICATIONS

Pease, Ann Caviani et al., "Light–generated oligonucleotide arrays for rapid DNA sequence analysis," *Proc. Natl. Acad. Sci. USA* 91:5022–5026 (1994).

Pope, Niedre M. et al., "New Application of Silane Coupling Agents for Covalently Binding Antibodies to Glass and Cellulose Solid Supports," *Bioconjugate Chem.* 4:166–171 (1993).

Rasmussen, Søren Richard et al., "Covalent Immobilization of DNA onto Polystyrene Microwells: The Molecules Are Only Bound at the 5' End," *Analytical Biochemistry* 198:138–142 (1991).

Saiki, Randall K. et al., "Genetic analysis of amplified DNA with immobilized sequence–specific oligonucleotide probes," *Proc. Natl. Acad. Sci. USA* 86:6230–6234 (1989).

Southern, E.M. et al., "Analyzing and Comparing Nucleic Acid Sequences by Hybridization to Arrays of Oligonucleotides: Evaluation Using Experimental Models," *Genomics* 13:1008–1017 (1992).

Steiner, Ulrich B. et al., "Self–Assembled Layers of Substituted Poly(p–phenylene)s on Gold and Copper," *Langmuir* 10:1164–1170 (1994).

Aizawa et al., Nippon Kagaku Kaishi, 11:2210–2213.

FIG.4

AMINO    NON AMINO

A without KOH,NCO
imidazole, toluene

37°c 2 hrs

B without KOH,NCO
imidazole, THF

A

37°c 15 min

B

A

RT 15 min

B untreated slide non amino    amino

3  NCO/DMSO (dry)/Imida

2  NCO/DMSO (comm)/Imida 1   untreated slide

- · WT probes
- · MM probes
- · WT probes

FIG. 13

METHOD FOR IMMOBILIZATION OF MOLECULES ON PLATINUM SOLID SUPPORT SURFACES

STATEMENT OF GOVERNMENT RIGHTS IN THE INVENTION

Part of the work performed during development of this invention utilized U.S. Government funds. The U.S. Government therefore has certain rights in the invention.

FIELD OF THE INVENTION

This invention is in the field of organic chemistry as related to the immobilization of molecules on solid surfaces and the molecular recognition of such molecules by ligands in hybridization or binding assays.

BACKGROUND OF THE INVENTION

Solid supports containing immobilized molecules have been extensively used in research, in clinical analyses and in the commercial production of foods and chemicals (see e.g., U.S. Pat. No. 5.153,166, issued Oct. 6, 1992); Akashi et al., *Bioconjugate Chem.* 3:363–365 (1992)). Immobilized nucleic acids are used in hybridization assays (Lamture et al., Nucl. Acids Res. 22:2121–2125 (1994)) and immobilized proteins in radioimmuno or ELISA assays (see, U.S. Pat. No. 5,314,830, issued May 24, 1994). In addition, enzymes have been immobilized to facilitate their separation from product and to allow for their efficient and repetitive use.

There are a number of important considerations in the development of an effective immobilization procedure. First, the procedure must minimize non-specific adsorption of molecules. Ideally, it should result in a surface which binds nothing but the target of the immobilized molecule. Second, the procedure must maintain the functional integrity of the immobilized molecules. An immobilization procedure which destroys the ability of a ligand to recognize and bind its natural target is of little or no practical value. A third factor of importance is the stability of the bond between the support and the immobilized molecule. Non-covalently attached molecules tend to leach off supports during assays, thereby reducing accuracy and sensitivity. Finally, the efficiency of the procedure must be carefully considered. Inefficient coupling of molecules will reduce the cost effectiveness of a procedure and may result in a support with a low binding capacity for target molecules. Assays which utilize such supports are likely to have a poor sensitivity.

Traditional supports used for immobilizing nucleic acids include nitrocellulose membranes, nylon membranes, avidin modified beads, dextrans and polysaccharides. Carbodiimide has been used for immobilizing nucleic acids on paper, latex, glass, dextrans and polystyrene. In addition, bromoacetyl and thiol-derivatized oligonucleotides have been immobilized on sulfhydryl- and bromoacetyl-polyacrylamide supports.

Recent interest in the development of biosensors and bioelectronic devices has required the development of immobilization procedures which are compatible with materials that have not traditionally been used for immobilizing biomolecules (Lamture et al., *Nucl. Acids Res.* 22:2121–2125 (1994)). These procedures must result in devices which are capable of performing reliable and sensitive assays in a cost-effective manner. The present application is directed to procedures which accomplish this goal.

RELATED ART

There are several United States patents which disclose methods related to the immobilization or derivatization of molecules. Several of the most relevant are as follows:

U.S. Pat. No. 5,001,051, issued Mar. 19, 1991, suggests that diisothiocyanate may facilitate the attachment of DNA to the surface of glass beads.

U.S. Pat. No. 4,414,323, issued Nov. 18, 1983. describes an assay in which the substrate of an enzyme is linked to a chemical group capable of developing a photographic film. The patent suggests, inter alia, linking amino groups by means of isocyanates, diisocyanates, or thiocyanates and recites a number of examples.

U.S. Pat. No. 5,241,012, issued Aug. 31, 1993, suggests nitrating polystyrene surfaces and then converting the bound nitro moieties into amino groups. Once formed, the amino groups can be "functionalized to provide various reactive functionalities, such as isocyanate, urethanes, cyanamides, or the like, where the functionality may be reacted with alcohols, amines, or thiols to form urethanes and ureas."

U.S. Pat. No. 4,098,645, issued Jul. 4, 1978, suggests reacting polyurethane polymers with isocyanates and then attaching molecules such as proteins.

U.S. Pat. No. 4,414,325, issued Nov. 8, 1983, contains a general suggestion that amino groups may be derivatized using isocyanates or thiocyanates and suggests a number of specific compounds that can be used in performing derivatizations.

In addition to the patents listed above, a number of journal publications have disclosed methods for immobilizing molecules. Among those related to the present application are publications describing the immobilization of molecules on glass or platinum using thiol-terminal silanes and heterobifunctional crosslinkers (Bhatia, et al., *Sensors and Actuators B*, 3:311–317 (1991)); the use of silane coupling agents for covalently binding molecules to glass or cellulose supports (Pope, et al., *Bioconjugate Chem.* 4:166–171 (1993)); the immobilization of DNA on polystyrene surfaces by phosphoramidate bonds (Rasmussen, et al., *Anal. Biochem.* 198:138–142 (1991)); and the covalent binding of oligonucleotides to polyacrylamide supports by thioether linkages (Fahy, et al., *Nucl. Acids Res.* 21:1819–1826 (1993)).

SUMMARY OF THE INVENTION

The present invention is directed to methods for immobilizing molecules on surfaces of platinum, glass, or aminated polypropylene. Molecules bearing an amino group or functionality are immobilized on platinum surfaces by first reacting such surfaces with either an isocyanate or an isothiocyanate to produce immobilized reactive moieties on the surface. These reactive moieties are then reacted with the molecule to form a covalent bond. Preferably, the platinum surface is reacted with a diisothiocyanate such as 1,4-phenylene diisothiocyanate. The present invention also encompasses devices having platinum surfaces made by the method described above.

In a second aspect, the invention is directed to a method for immobilizing nucleic acids on a platinum surface. This is accomplished by first reacting the surface with either an isocyanate or an isothiocyanate and then with a nucleic acid derivatized to contain an amino group. It has been shown that favorable results may be obtained by reacting the platinum surface with a diisothiocyanate such as 1,4-phenylene diisothiocyanate. The preferred method for forming the covalent bond between nucleic acid and immobilized moieties on the platinum surface is by performing reactions at room temperature, about 25° C., for approximately 15 to 20 minutes, using a nucleic acid concentration of between 10 and 20 µM. Devices having platinum surfaces containing nucleic acids immobilized by the procedures above are claimed as part of the invention.

In a third aspect, the invention is directed to a method for immobilizing a nucleic acid on a glass surface. This is accomplished in two steps. First, the glass surface is reacted with a solution comprising an organic solvent, and a derivatizing agent (either an isocyanate or an isothiocyanate). Second, the glass surface is reacted with an oligonucleotide derivatized to contain an amino group. In a preferred embodiment, imidazole is included in the first step of the immobilization procedure. Regardless of whether imidazole is included, the preferred organic solvent is dimethyl sulfoxide. Diisocyanates, especially 1,3-phenylene diisocyanate, have been found to produce favorable results. Devices having a glass surface prepared in the manner described above are also claimed.

The invention is also directed to a method for immobilizing a nucleic acid on a surface of aminated polypropylene. Again, this is accomplished in two steps. First, the polypropylene surface is derivatized by reaction with a derivatizing agent (either an isocyanate or an isothiocyanate) dissolved in a solution of dimethyl formamide/pyridine. In the second step, the surface is reacted with a nucleic acid derivatized to contain an amino group. It is preferred that 1,4-phenylene diisothiocyanate be used in the first step to derivatize the polypropylene surface. Devices having aminated polypropylene surfaces, modified by the method described above to contain immobilized nucleic acid, are also claimed.

BRIEF DESCRIPTION OF THE FIGURES

FIG. 1 shows schematically the chemical reactions involved in the immobilization of DNA on a platinum surface. The jagged lines linking the platinum surface to phenyl rings indicate that the exact chemical linkage is not known with certainty.

FIG. 2 (panel A), is a graphical representation of the attachment of amino-derivatized oligonucleotide probes to a platinum surface as a function of time. Prior to attachment, the platinum surface was reacted with 1,4-phenylene diisothiocyanate. As shown in the figure, attachment was examined at oligonucleotide concentrations of 10 µM, 20 µM, 50 µM and 100 µM. FIG. 2 (panel B), shows the same results wherein the amount of probe attached is expressed as a percentage of the total amount of probe applied to the surface. FIG. 2, panel C, shows the results that were obtained when reactions were carried out using ordinary (i.e., non-derivatized) oligonucleotides in the place of amino-derivatized oligonucleotides. FIG. 2, panel D, depicts the same results shown in 2B wherein probe attachment is expressed as a percentage applied to the platinum surface.

FIG. 4. FIG. 4 shows the results of a hybridization experiment performed on a platinum surface containing immobilized probes. Platinum surfaces were derivatized using 1,4-phenylene diisothiocyanate and were then reacted with either amido-derivatized or non-derivatized oligonucleotide probes at concentrations of 10 µM, 20 µM, 50 µM or 100 µM. Immobilized probes were hybridized to complementary target oligonucleotides. Hybridizations were performed in 6× saline sodium titrate (SSC) at 6° C. overnight. Plates were washed with hybridization buffer and then exposed to a phosphor imaging plate for a period of 30 minutes.

FIG. 5 is a bar graph representing the percent hybridization density that was obtained by hybridizing target oligonucleotides to platinum surfaces that had been reacted with amino-derivatized probes at concentrations of 10 µM, 20 µM, 50 µM and 100 µM. Hybridizations were performed either in the presence of 3.3 molar tetramethyl ammonium chloride (TMAC) or 6× saline sodium citrate (SSC). The procedure for determining percentage hybridization density was the same as for FIG. 3.

FIG. 6 represents the results of an experiment that was the same as that described above for FIG. 5, but where platinum surfaces had been prepared using probes that were not derivatized to contain amino groups.

FIG. 7 is a schematic representation showing the derivatization of glass surfaces using 1,3-phenylene diisocyanate and the subsequent reaction of immobilized groups with amino-derivatized oligonucleotides.

FIG. 12 is a schematic representation of the derivatization of an aminated polypropylene surface with 1,4-phenylene diisothiocyanate followed by attachment of amino-derivatized oligonucleotide probes.

FIG. 13. Aminated polypropylene surfaces were reacted with 1,4-phenylene diisothiocyanate and the surfaces were then incubated with amino-derivatized oligonucleotide probes. Two types of probes were used: wild type ("WT") probes (5'-TGGAGGTGA) and mismatched ("MM") probes (either 5'-TGGAGGTTA or 5'-TAGAGGTGA). Incubation proceeded at 65° C. for a period of 2.5 hours. The reacted polypropylene films were washed with water and 30% ammonia and were then hybridized with labelled target DNAs having nucleotide sequences complementary to the WT probes (5'-TGTGACTCACCTCCAGTTGCT). After incubation and washing, films were exposed to a phosphor imaging plate for a period of 25 minutes.

FIG. 14 (panel A), shows the results of a hybridization performed between oligonucleotide probes that had been immobilized on a surface of aminated polypropylene and labelled target oligonucleotides containing complementary nucleotide sequences. Amino-derivatized probes were attached at concentrations of 10 µM, 20 µM, 50 µM or 100 µM. Hybridizations were performed either in the presence of tetramethyl ammonium chloride (TMAC) or in the presence of saline sodium citrate (SSC). FIG. 14 (panel B), shows the results obtained when the same experiment was performed using polypropylene films with immobilized non-derivatized probes at the same concentrations.

DEFINITIONS

Figure 1:
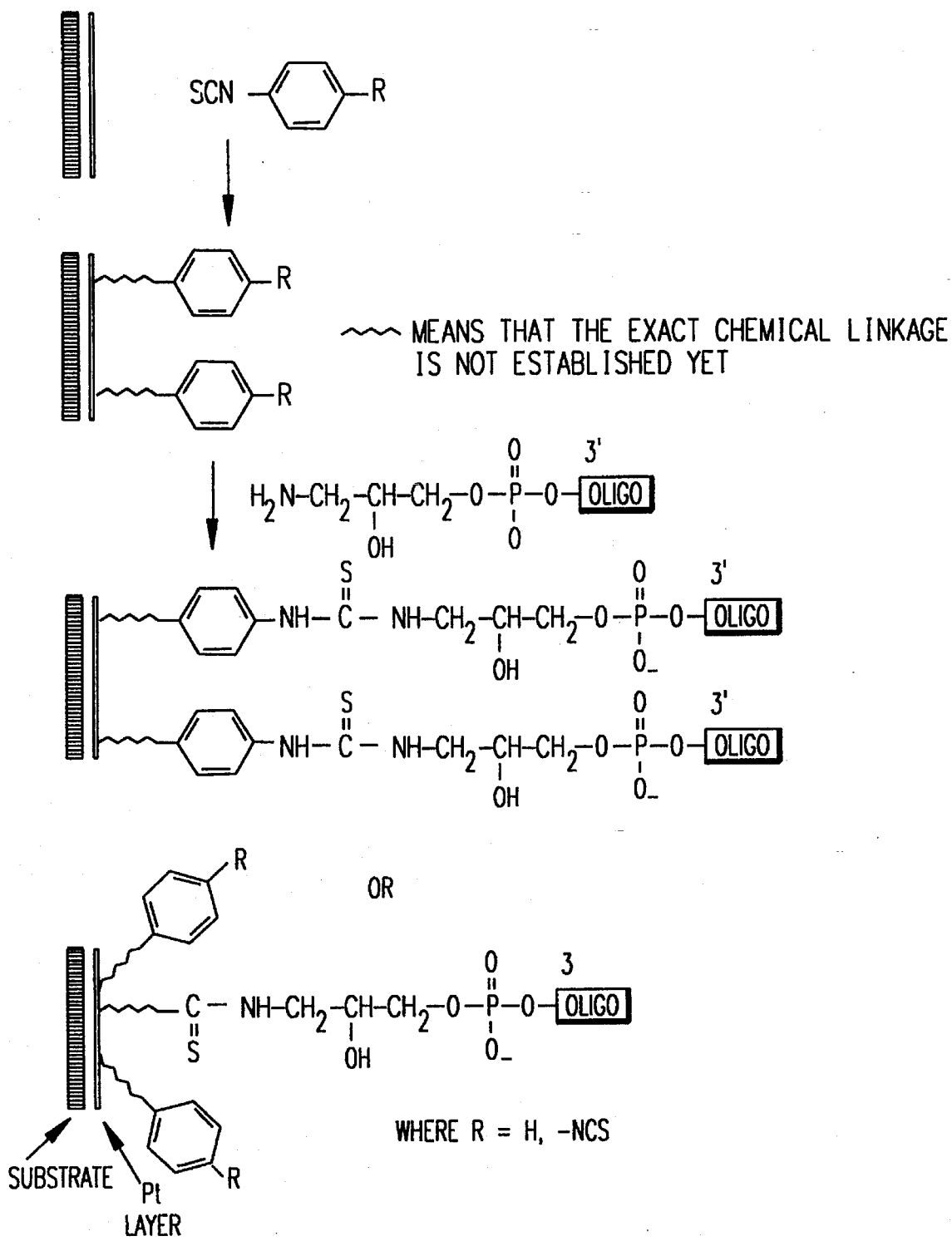
FIG. 1.
Figure 2A:
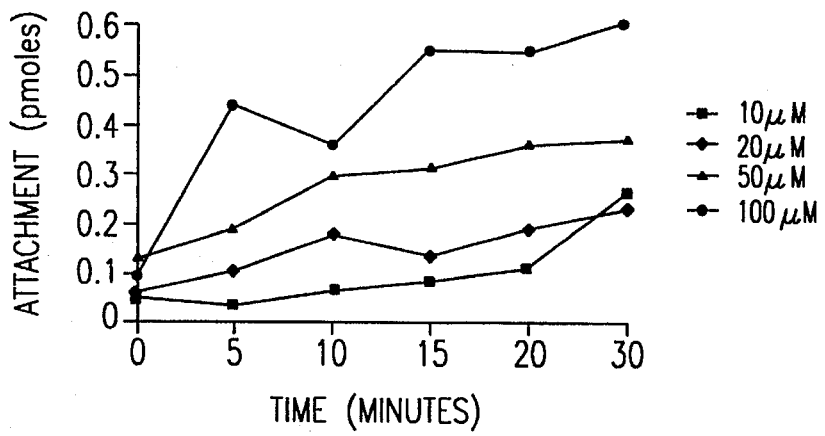
FIG. 2 (panel A)–FIG. 2 (panel D).
Figure 2B:
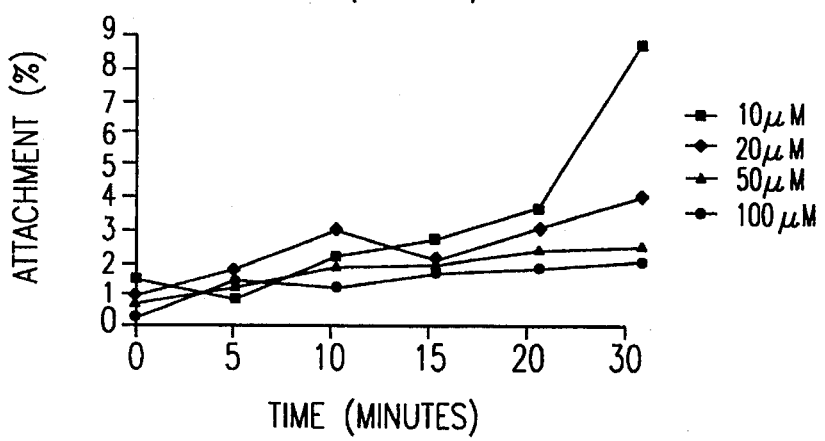
Figure 2C:
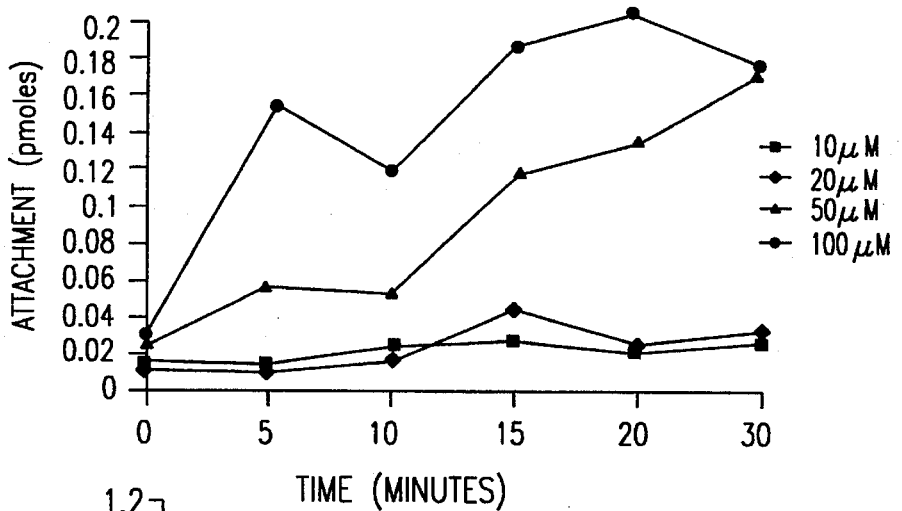
Figure 2D:
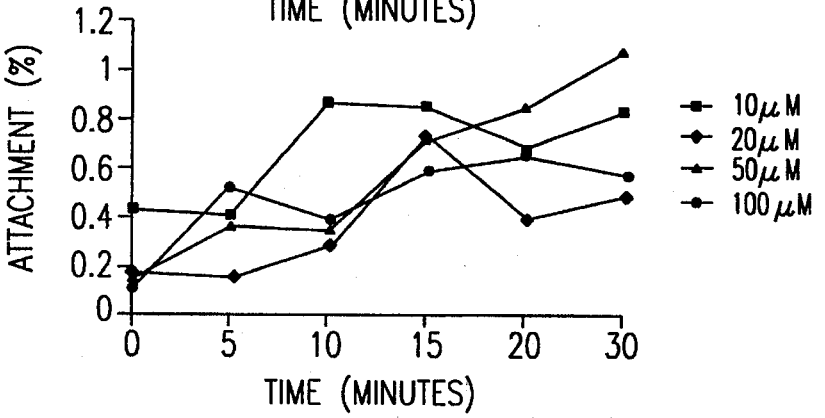

In order to provide a clear and consistent understanding of the specification and claims, including the scope to be given to the terms used therein, the following definitions are provided.

Isocyanate:

The isocyanate group is represented chemically as: R—N=C=O and is the isomeric form of cyanate, —O—C≡N; where R is an alkyl or aryl group.

Diisocyanate:

The diisocyanate group is represented chemically as: O=C=N—R—N=C=O; where R is an alkyl or aryl group.

Isothiocyanate:

The isothiocyanate group is represented chemically as: R—N=C=S; where R is an alkyl or aryl group.

Diisothiocyanate:

As the name indicates, a diisothiocyanate is a chemical compound comprising two isothiocyanate groups. It may be represented chemically as: S=C=N—R—N=C=S; where R is an alkyl or aryl group.

Oligonucleotide:

As used herein, the term oligonucleotide refers to a nucleic acid having at least 2 joined nucleotides. It is not intended that the term otherwise limit the number of nucleotides. Thus, for the purposes of the present application, it may be considered synonymous with nucleic acid strand.

Probe:

As presently used, the term "probe" refers to short oligonucleotides which are immobilized on a solid surface and then used to recognize and bind nucleic acids with complementary sequences in hybridization assays. Unless otherwise specified, wild type probes were used in the experiments described herein and had the sequence:

5'-TGGAGGTGA (wild type probe).

Two other probes that were used each contained one nucleotide mismatch relative to the above wild type probes. These were as follows:

5'-TGGAGGTTA (mut 549 probe);

and

5'-TAGAGGTGA (mut 551 probe)

Target oligonucleotide:

The term "target oligonucleotide" refers to the nucleic acids which have a nucleotide sequence sequences complementary to that of the probe and which may be recognized and bound by probes in hybridization assays. Unless otherwise specified, the target oligonucleotide used in the experiments described herein had a sequence as follows:

5'-TGTGACTCACCTCCAGTTGCT (wild type target)

DETAILED DESCRIPTION OF THE INVENTION

In the following description, reference will be made to various methodologies well-known to those skilled in the arts of organic chemistry, biochemistry and molecular biology. Standard reference works setting forth general principles of these disciplines are: March, J., *Advanced Organic Chemistry, Reactions, Mechanisms and Structure*, 3rd edition, John Wiley & Sons, Inc., New York (1985); Maniatis, T, et al., *Molecular Cloning, A Laboratory Manual*, Cold Spring Harbor Laboratories, Cold Spring Harbor, N.Y. (1982)); and Hames, B. D., et al., Nucleic Acid Hybridization, A Practical Approach, IRL Press, Washington, D.C. (1985).

I. Immobilization of Molecules on Platinum

A. Description of the Immobilization Procedure

The present invention is directed, inter alia, to a method for immobilizing amino-containing molecules on platinum surfaces. The experiments described herein utilized small platinum wafers obtained from the Lincoln Laboratories of the Massachusetts Institute of Technology, however, other platinum surfaces will work equally well.

The chemical reactions involved in the immobilization procedure are shown in FIG. 1. Surfaces are first cleaned thoroughly using organic solvents. The preferred wash procedure is to sonicate surfaces sequentially in hexane, acetone and ethanol for a period of 10 minutes each. After the final sonication, the washed surface is dried and then reacted with a derivatizing agent, either an isocyanate or an isothiocyanate. A 1.5% solution of 1,4-phenylene diisothiocyanate dissolved in dimethyl formamide-pyridine (90:10) has been found to produce favorable results.

After reaction, excess derivatizing agent is washed away with dimethyl formamide and surfaces are dried. The immobilized groups present on the platinum surface as the result of the aforementioned reaction are available to react with any molecule that has, or can be modified to have, an amino group. A wide variety of conditions can be employed for the immobilization procedure. In the case of amino-derivatized oligonucleotides, an incubation at room temperature, about 25° C., for 15 to 20 minutes with an oligonucleotide concentration of 10 μM has been found to produce suitable results.

The surface containing the immobilized molecule is washed and used in binding assays. Any type of standard binding assay can be used (see e.g., U.S. Pat. No. 5,314,830, issued May 24, 1994 and references cited therein). For example, mobilized antibodies could be reacted with samples containing antigen and resulting antibody-antigen complexes could be identified using a labelled second antibody. Alternatively, ligands may be immobilized and used to measure receptor levels. In the case of immobilized nucleic acids, the ability of probes to hybridize to complementary sequences of labelled or DNA or RNA may be determined.

B. Examples Illustrating the Procedure

The following detailed guidance is provided concerning experimental protocols used in experiments concerned with the immobilization of molecules on platinum surfaces. Unless otherwise noted, these were the protocols used in the experiments described above.

Cleaning of Platinum Chips

Platinum chips are cleaned by sequential sonication in hexane, acetone and ethanol. Each sonication proceeds for a period of 10 minutes. After the final sonication, platinum chips are air dried.

Modification of Platinum Surface

A solution for the derivatization of platinum surfaces may be prepared by dissolving 15 mg of 1,4-phenylene diisothiocyanate in dimethyl formamide (0.9 ml) and then adding pyridine (0.1 ml). The solution is mixed well and then applied to a clean platinum chip that has been placed in a petri dish inside a vacuum desiccator. The solution is applied with a glass dropper so that the platinum surface is completely covered and a slight vacuum is then applied to the desiccator. After 5 hours, the platinum chip is washed with dimethyl formamide, 4 or 5 times, and then with acetone, 3 times. After the final wash, the chip is allowed to air dry.

Probe Attachment

Oligonucleotide probes (typically 10 μM–100 μM) are dissolved in water and then spotted on a platinum surface (typically 300 nl per spot). The platinum chip is kept at room temperature for about 15 minutes. At the end of this time, it is washed with distilled water (15 minutes); with 30% ammonia (2 lots incubated for 30 minutes each); and again with water (15 minutes). Washing is accomplished by incubating the platinum chip in a container partially filled with wash solution and gently mixing for the designated time. After the final wash, the platinum chip is allowed to air dry at room temperature.

Hybridization

For an array of probes covering approximately 2 square centimeters of surface or less, 40 μl of hybridization buffer is used. This is prepared by taking 0.6 μl of a stock solution of target oligonucleotide present at a concentration of 1 μmole per μl. The final amount of target oligonucleotide in 40 μl will therefore be 600 femtomoles. The following additional components are then added;

| tetramethyl ammonium chloride | TMAC (5M) | 26.4 μl |
|---|---|---|
| ethylenediamine tetraacetic acid | EDTA (50 mM) | 1.6 μl |
| | Tris (1M) | 2 μl |
| sodium dodecyl sulphate | SDS (2%) | 2 μl |
| polyethylene glycol | PEG (40%) | 8 μl |

The hybridization buffer with the above components is prepared by first drying the 0.6 μl of concentrated target solution under a vacuum. To the dry oligonucleotide, is added 26.4 μl of 5M TMAC; 2 μl of 1M Tris; and 1.6 μl of 50 mM EDTA. The combined solutions are mixed well and then 2 μl of 2% SDS and 8 μl of 40% PEG are added. The final solution is mixed well before using.

The oligonucleotides in the above hybridization buffer are allowed to denature at 90° C. for 4 minutes. The hot solution is then directly applied to the probes immobilized on a platinum surface and the preparation is covered with a cover slip. Hybridization proceeds at 6° C. overnight.

After the incubation is complete, the cover slip is removed from the platinum surface and the chip is washed, at room temperature, with hybridization solution that contains the components described above except for oligonucleotide and PEG. Hybridized target oligonucleotide may then be visualized by exposing surfaces to a phosphor imaging plate and the amount of radioactivity present at each location on the plate may be quantitated using a phosphorimager. If desired, background radiation on a platinum surface may be further reduced by again washing platinum surfaces in hybridization solution at room temperature for 20–30 minutes.

In some experiments, hybridization was performed in buffer containing saline sodium citrate (SSC) rather than TMAC. Hybridization buffer containing 6× SSC may be prepared by combining the following stock solutions:

| target oligo (1 μmol/μl) | 0.6 μl (without drying) |
|---|---|
| SSC (20×) | 12 μl |
| SDS (2%) | 10 μl |
| PEG (40%) | 8 μl |
| distilled water | 9.4 μl |

Hybridizations in 6× SSC follow the same incubation and washing procedures as described above.

EXPERIMENT 1

Immobilization Of DNA on a Platinum Surface as a Function of Time and Probe Concentration Platinum chips were obtained from the Lincoln Laboratories, Massachusetts Institute of Technology, and cleaned with hexane, acetone and ethanol by sonication (10 minutes for each solvent). After the final wash, chips were dried at room temperature.

A 1.5% solution of 1,4-phenylene diisothiocyanate was prepared in dimethyl formamide-pyridine (90:10) and allowed to cover the chip surface overnight in a desiccator. The chips were then washed sequentially in dimethyl formamide and acetone and dried at room temperature. Oligonucleotide probes labelled with $^{32}P$ were incubated with the isothiocyanate-derivatized platinum surface at room temperature for varying periods of time. Both amino-derivatized oligonucleotide probes and non-derivatized probes were reacted at oligonucleotide concentrations of 10 μM, 20 μM, 50 μM and 100 μM. Oligonucleotides modified to contain amino groups were purchased commercially from Genosys Biotechnologies, Woodlands. Alternatively, oligonucleotides containing such terminal amino groups can be prepared using a controlled pore glass support with a 3'-amino modifier, purchased from Glen Research. The non-derivatized probes provide an estimate of the extent to which oligonucleotides attach to sites other than terminal amino groups, (attachment probably occurs to the ring nitrogens of nucleotides).

After incubations were complete, platinum chips were washed with water (15 minutes), two lots of 30% ammonia (total time 1 hour), and again with water (15 minutes). Washed chips were dried at room temperature and the amount of retained radioactivity determined using a phosphorimager. Results are shown in Tables 1 and 2.

TABLE 1

BINDING OF AMINO PROBES TO ISOTHIO-CYANATE-DERIVATIZED PLATINUM SURFACES

| Probe Concentration | Incubation Time (min.) | Percent Bound | pmoles Bound |
|---|---|---|---|
| 10 μM | 0 | 1.56 | 0.047 |
|  | 5 | 0.87 | 0.026 |
|  | 10 | 2.15 | 0.065 |
|  | 15 | 2.72 | 0.082 |
|  | 20 | 3.60 | 0.108 |
|  | 30 | 8.70 | 0.260 |
| 20 μM | 0 | 0.99 | 0.059 |
|  | 5 | 1.74 | 0.104 |
|  | 10 | 2.99 | 0.179 |
|  | 15 | 2.10 | 0.126 |
|  | 20 | 3.08 | 0.184 |
|  | 30 | 4.02 | 0.241 |
| 50 μM | 0 | 0.83 | 0.124 |
|  | 5 | 1.25 | 0.187 |
|  | 10 | 1.96 | 0.294 |
|  | 15 | 2.10 | 0.315 |
|  | 20 | 2.44 | 0.366 |
|  | 30 | 2.44 | 0.366 |
| 100 μM | 0 | 0.31 | 0.093 |
|  | 5 | 1.46 | 0.438 |
|  | 10 | 1.18 | 0.354 |
|  | 15 | 1.82 | 0.546 |
|  | 20 | 1.82 | 0.546 |
|  | 30 | 1.99 | 0.597 |

TABLE 2

BINDING OF NON-AMINO PROBES TO ISO-THIOCYANATE-DERIVATIZED PLATINUM SURFACES

| Probe Concentration | Incubation Time (min.) | Percent Bound | pmoles Bound |
|---|---|---|---|
| 10 μM | 0 | 0.44 | 0.013 |
|  | 5 | 0.40 | 0.012 |
|  | 10 | 0.87 | 0.026 |
|  | 15 | 0.86 | 0.026 |
|  | 20 | 0.68 | 0.020 |
|  | 30 | 0.84 | 0.025 |
| 20 μM | 0 | 0.18 | 0.011 |
|  | 5 | 0.15 | 0.009 |
|  | 10 | 0.29 | 0.017 |
|  | 15 | 0.75 | 0.045 |
|  | 20 | 0.39 | 0.023 |
|  | 30 | 0.50 | 0.030 |
| 50 μM | 0 | 0.17 | 0.026 |
|  | 5 | 0.37 | 0.056 |
|  | 10 | 0.34 | 0.051 |
|  | 15 | 0.75 | 0.112 |
|  | 20 | 0.86 | 0.129 |
|  | 30 | 1.09 | 0.163 |
| 100 μM | 0 | 0.12 | 0.036 |
|  | 5 | 0.50 | 0.150 |
|  | 10 | 0.38 | 0.114 |
|  | 15 | 0.60 | 0.180 |
|  | 20 | 0.65 | 0.195 |
|  | 30 | 0.56 | 0.168 |

The percentages shown in the above tables were based upon the total amount of photostimulable light units placed on chips in a given experiment. This was determined by spotting the platinum surface with labelled oligonucleotide probes but not washing the surface prior to quantitation by phosphorimager. The results indicate that a reaction time of 15 minutes is sufficient to allow most covalent coupling to occur. A significant percentage of the probes became attached to surfaces at all of the concentrations examined and, in each case attachment of non-amino probes could be minimized by limiting reaction time to under 10 minutes.

FIG. 2, panels A to D, show in graphical form, the results obtained from the above experiment. Ideally, reaction conditions should be selected which maximize the binding of amino-derivatized probes relative to the attachment of non-derivatized probes. Based upon the results shown in the figure, it was decided that best results could be obtained by performing reactions at a probe concentration of 10–20 μM for about 15 to 20 minutes at room temperature. As will be seen in Experiment 2 below, incubations performed at other temperatures do not lead to substantially different results.

EXPERIMENT 2

Attachment of Oligonucleotide Probes to a Platinum Surface as a Function of Time and Temperature Platinum chips were prepared using phenylene diisothiocyanate as described above. The chips were then reacted with $^{32}P$ labelled amino-derivatized and non-derivatized oligonucleotide probes present at a concentration of 10 μM. The reaction was performed at 6° C., 15° C., 37° C. and 65° C. for a period of 10–30 minutes. The percentage of probes attached under each reaction condition was determined as described in Experiment 1 and results are shown in Tables 3 and 4.

TABLE 3

ATTACHMENT OF AMINO PROBES AS A FUNCTION OF TIME AND TEMPERATURE

| Temperature | Time (min.) | Percentage of Total Probes Attached |
|---|---|---|
| 6° C. | 10 | 4.45 |
|  | 15 | 4.32 |
|  | 20 | 3.67 |
|  | 30 | 4.13 |
| 15° C. | 10 | 1.13 |
|  | 15 | 2.94 |
|  | 20 | 3.34 |
|  | 30 | 5.48 |
| 37° C. | 10 | 3.01 |
|  | 15 | 6.3 |
|  | 20 | 4.3 |
|  | 30 | 4.7 |
| 65° C. | 10 | 4.2 |
|  | 15 | 3.4 |
|  | 20 | 5.4 |
|  | 30 | 3.3 |

TABLE 4

ATTACHMENT OF NON-AMINO PROBES AS A FUNCTION OF TIME AND TEMPERATURE

| Temperature | Time (min.) | Percentage of Total Probes Attached |
| --- | --- | --- |
| 6° C. | 10 | 0.43 |
|  | 15 | 0.67 |
|  | 20 | 0.64 |
|  | 30 | 0.63 |
| 15° C. | 10 | 0.23 |
|  | 15 | 0.84 |
|  | 20 | 0.66 |
|  | 30 | 1.05 |
| 37° C. | 10 | 0.90 |
|  | 15 | 0.46 |
|  | 20 | 0.44 |
|  | 30 | 0.29 |
| 65° C. | 10 | 0.52 |
|  | 15 | 0.29 |
|  | 20 | 0.47 |
|  | 30 | 0.39 |

One conclusion that may be drawn from the above results is that good attachment occurs at all of the temperatures examined. Thus, for convenience, reactions may be performed at room temperature, i.e., at about 25° C. It appeared that the majority of attachment of amino-probes had occurred before 15 minutes of incubation. Overall, it has been found that the attachment of probes via sites other than terminal primary amino groups, as evidenced by the attachment of non-derivatived oligonucleotides, can be minimized by using relatively short reaction times.

EXPERIMENT 3

Hybridization of Immobilized Probes to Target DNA Under Conditions of Low Stringency The optimum conditions for immobilizing probes on platinum surfaces depends not only upon the total percentage of probe attached but also upon the ability of attached probes to specifically hybridize target DNAs with complementary nucleotide sequences. In order to examine specificity of hybridization as a function of probe concentration, platinum chips were reacted with 1,4-phenylene diisothiocyanate as described in Experiment 1. Amino-derivatized and non-derivatized probes were reacted at room temperature for 30 minutes at concentrations of 10 µM, 20 µM, 50 µM and 100 µM. After probe attachment, chips were washed using water and 30% ammonia. Immobilized probes were then hybridized to $^{32}$P-labelled target DNAs containing complementary base sequences. Hybridization was preformed in buffer containing tetramethyl ammonium chloride at 6° C. overnight.

Figure 3:
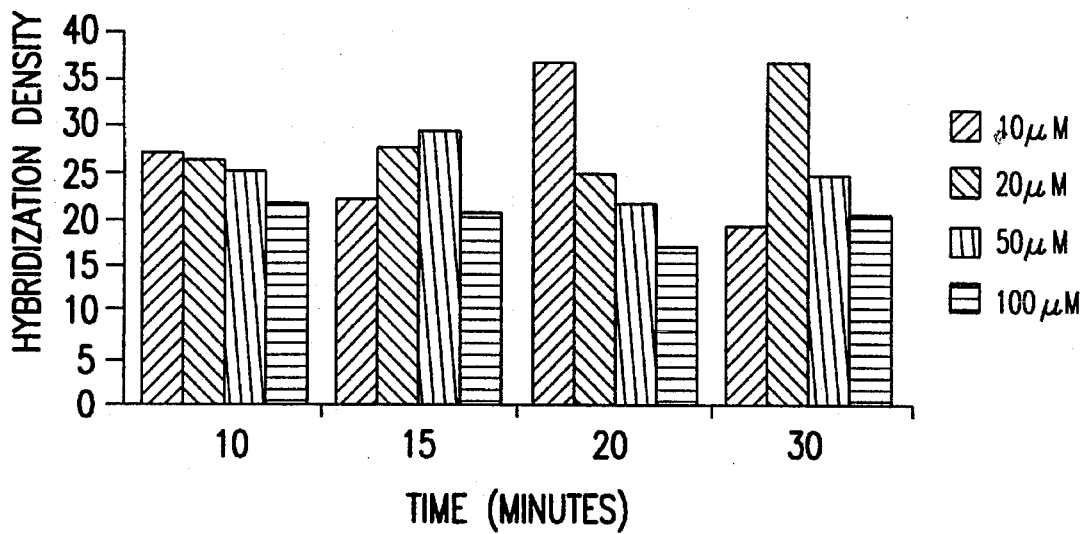
FIG. 3. Hybridizations were carried between $^{32}$P-labelled target DNA and probes that had been immobilized on the surface of platinum chips. Surfaces were prepared using probes at concentrations of 10 µM, 20 µM, 50 µM and 100 µM. Labelled target DNA was allowed to hybridize with the prepared chips which were then washed with water and 30% ammonia. The amount of probe retained on each surface was determined using a phosphorimager and results were expressed in terms of photostimulable light units (PSLs). The number of PSLs obtained for each sample was divided by the total number of PSLs obtained for all samples and multiplied by 100 to obtain the percentages shown on the y-axis of the figure.

After incubation, chips were washed with hybridization buffer at room temperature for three hours. The amount of labelled target DNA bound at each position on the chip was determined based upon the number of photostimulable light units ("PSLs") measured using a phosphorimager (Fuji). The number of PSLs hybridized at each position was divided by the total PSLs present on the chip and multiplied by 100 to obtain the relative hybridization density for each probe concentration. The results of the experiment for amino-derivatized probes are shown as a bar graph in FIG. 3.

It can be seen that hybridization density was greatest when probes were attached at a concentration of between 10 and 20 µM. The reduced hybridization density seen at higher concentrations of probe may be due to stearic interference on surfaces, i.e., the probes may be too densely packed on the surface to allow ready access to the complementary target nucleic acids.

Under the hybridization conditions employed in this experiment, i.e., at low stringency significant hybridization between target DNA and non-derivatized probes occurred. Hybridization density was approximately 8% when non-derivatized probes were immobilized at a concentration of 10 µM and rose to approximately 12% when the probes were immobilized at a concentration of 100 µM. It was found that under conditions of higher stringency, hybridization to amino-derivatized probes remained substantial but that hybridization to non-amino probes was almost entirely eliminated (see Experiment 4).

EXPERIMENT 4

Figure 5:
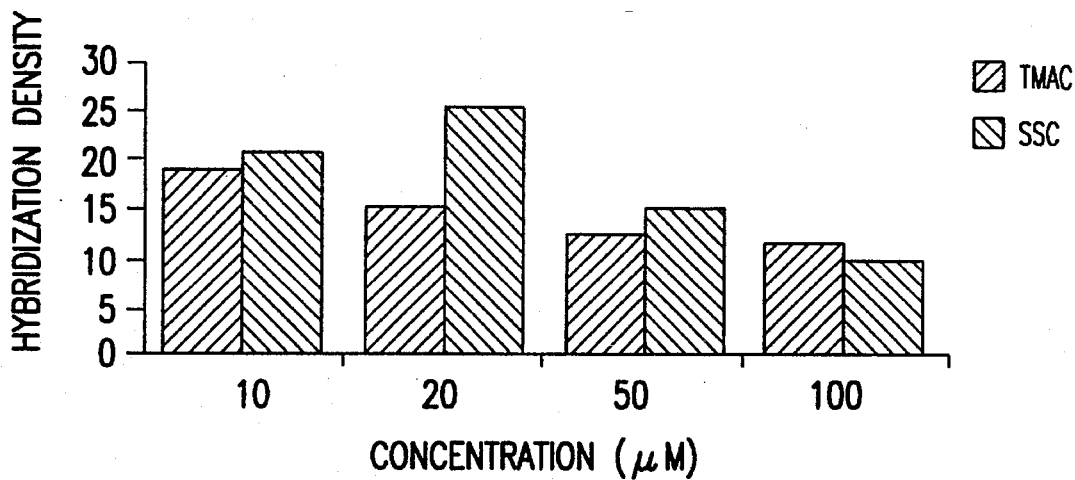
FIG. 5.
Figure 6:
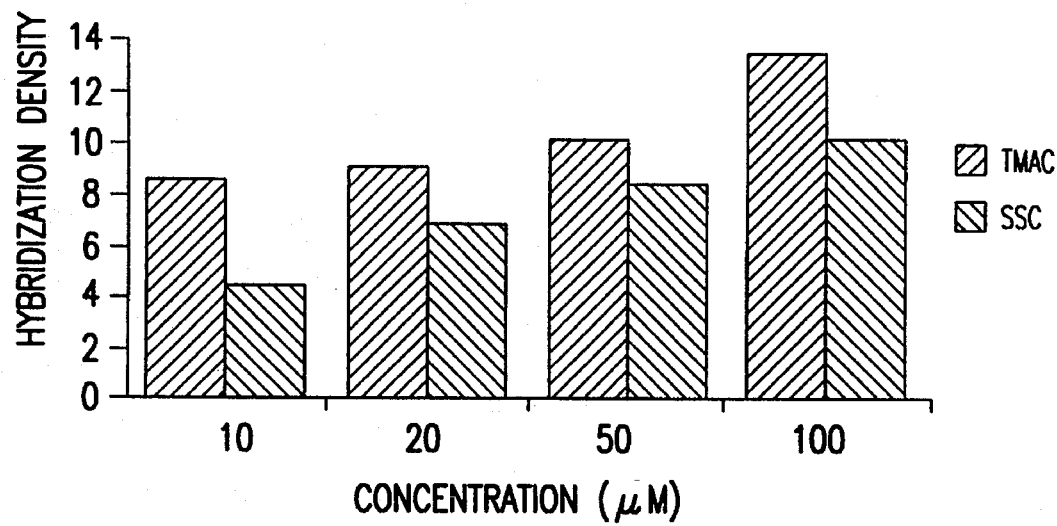
FIG. 6.
Figure 4:
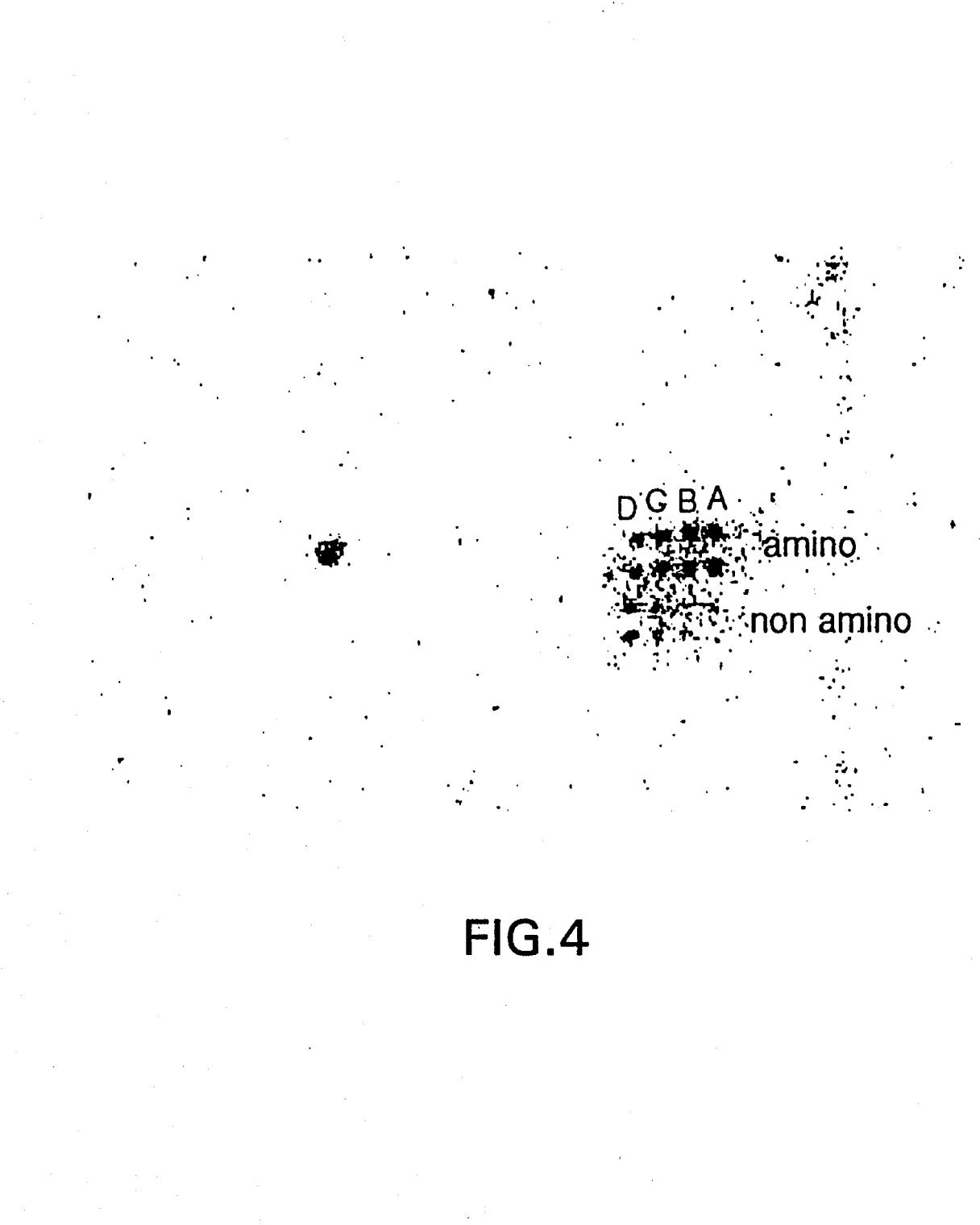

Hybridization of Immobilized Oligonucleotides Probes to Target DNA Under Conditions of High Stringency The hybridization experiment described above was repeated under conditions of higher stringency. Amino and non-amino probes were again attached at concentrations ranging from 10–100 µM. Attachment took place at 37° C. for a period of 30 minutes and plates were then washed using water and 30% ammonia. In other experiments, reactions were performed at room temperature for a period of 15 to 20 minutes and similar results were obtained. Labelled target DNA sequences were allowed to hybridize at 6° C. overnight, in a solution containing 6× saline sodium citrate (6× SSC). Plates were then washed in hybridization solution tbr 2 hours, dried, and exposed to a phosphor imaging plate. The results shown in FIG. 4 indicate that optimal hybridization occurs when amino-derivatized probes are immobilized at a concentration 10 or 20 µM. It can be seen that little or no significant hybridization occurred to non-amino probes immobilized at these concentrations. Hybridization density for the amino-derivatized probes was determined as before and results are shown in FIGS. 5 and 6. These figures indicate that maximum hybridization occurred when amino-derivatized probes were immobilized in a concentration range of 10 to 20 µM.

C. CONCLUSIONS

Figure 7:
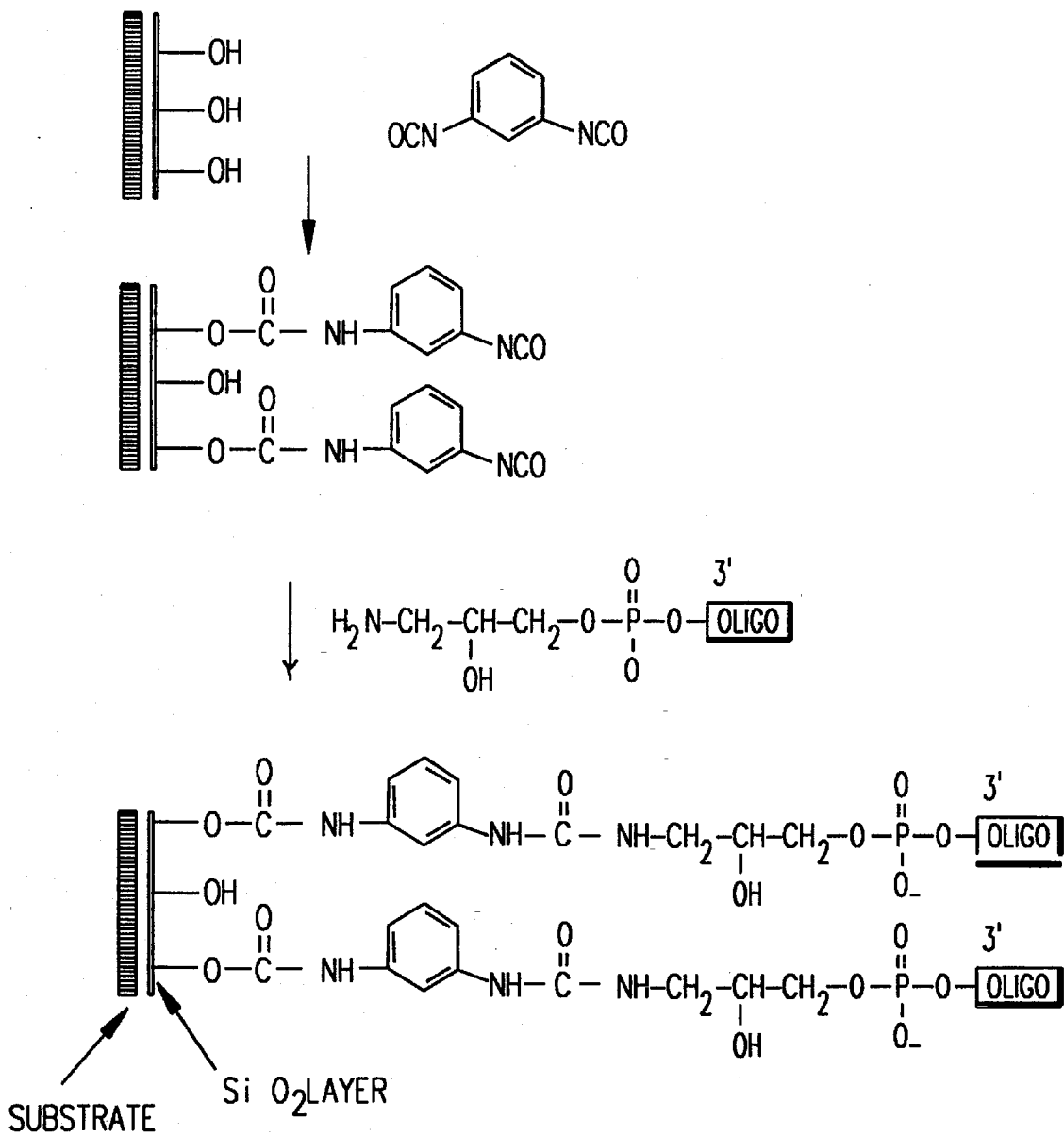
FIG. 7.

It was concluded from the above results that the treatment of platinum surfaces with isothiocyanates provided an effective means for covalently immobilizing amino-containing molecules. Using oligonucleotides, it was found that optimal results could be obtained when probes were attached at a concentration of 10–20 µM for a period of 15 to 20 minutes at room temperature, about 25° C. Under these conditions, the oligonucleotides retained the ability to specifically recognize their complementary target sequences and non-specific adsorption to plates was minimized. Since the chemical reactivity of isocyanates and isothiocyanates should be essentially the same under the conditions used in these experiments, it can be concluded that treatment of platinum surfaces with isocyanates should produce similar results. Also, variously substituted isocyanates or isothiocyanates, e.g., xylene diisothiocyanate, may be used II. Immobilization of Nucleic Acids on Glass Surfaces A. Description of the Immobilization Procedure A second aspect of the present invention is directed to the immobilization of amino-containing nucleic acids on glass (i.e., silicon dioxide) surfaces. FIG. 7 illustrates the basic reactions involved in the immobilization process using 1,3-phenylene diisocyanate as the agent for derivatizing the glass surface. Any type of glass surface may be used as a substrate, provided that it is adequately cleaned prior to derivatization. Washing with acid, followed by successive washings in water and organic solvents has been found to produce adequate results.

The washed surface is reacted (e.g., overnight at room temperature) with a derivatizing agent (either an isocyanate or an isothiocyanate) dissolved in an organic solvent. Although toluene and tetrahydrofuran have been found to be adequate solvents, greatly improved results are obtained when dimethyl sulfoxide is used. If solvents other than dimethyl sulfoxide are used, it is preferred that the solution contain imidazole. The ratio of imidazole to derivatizing agent is not critical, however a molar ratio of 1 mole of derivatizing agent to 2 moles of imidazole has been found to produce good results. When DMSO is used as the solvent, the presence of imidizole does not appear to be necessary for attachment to occur.

Glass surfaces containing immobilized reactive groups are washed with organic solvent (e.g., toluene or acetone) and then dried (e.g., at room temperature for 5–10 minutes). The glass surface may be kept dry by storage in a vacuum desiccator.

Surface-bound moieties react with the amino groups of amino-derivatized oligonucleotides to form a covalent urea linkage. In the case of immobilized isothiocyanate moieties, attachment occurs through covalent thiourea linkages. Reactions may be successfully performed at room temperature and are essentially complete within 30 minutes.

After attachment, immobilized oligonucleotides may be used in hybridization reactions with other nucleic acids. It has been found that oligonucleotide probes immobilized in the manner described above retain the ability to specifically recognize and bind target DNAs having complementary nucleotide sequences. Assay conditions may be varied to accomplish specific experimental objectives. For example, hybridization assays may be performed at different stringencies depending upon the extent to which the experimenter wants hybridization to occur to target nucleic acids having mismatched nucleotide sequences.

B. Examples Illustrating the Procedure

Unless otherwise noted, the following procedures were used in experiments examining the immobilization of nucleic acids on glass surfaces.

Cleaning of Glass Slides

Glass slides are cleaned by placing them in 1M $HNO_3$ for 30–40 minutes. After rinsing twice with water, slides were sonicated successively in solutions of hexane, acetone, and ethanol, 10 minutes per sonication. The washed slides were dried at 85° C. for 2 hours.

Modification of Slide Surface

Slide surfaces are modified using a solution of 1,3-phenylene diisocyanate. This is prepared by dissolving 16 mg of 1,3-phenylene diisocyanate in 30 ml of either dimethyl sulfoxide (dry) or toluene (dry). 14 mg of imidazole are then added. When toluene is used as the solvent, a suspension forms that may be disrupted by sonication. Alternatively the cloudy suspension may be used.

Clean, dry slides are covered with the diisocyanate solution and incubated in a sealed container overnight at room temperature. They are then transferred to a new container and washed twice with dimethyl sulfoxide and 3 times with acetone. Slides are dried at room temperature for 15–30 minutes and stored in a vacuum desiccator.

Probe Attachment

Slides (75 mm×25 mm×0.96–1.06 mm thick) are derivatized with 1,3-phenylene diisocyanate as described above. A 300 nl aliquot of oligonucleotide dissolved in water is applied to slides which are then incubated at room temperature for about 30 minutes. After incubation, the slides are washed in distilled water (15 minutes); twice in 30% ammonia (30 minutes each); and again in distilled water (15 minutes). After the final wash, slides are allowed to air dry at room temperature.

Hybridization

Hybridization of probes immobilized on glass slides utilized the same buffers and were performed using the same procedures as hybridization of probes immobilized on platinum surfaces.

EXPERIMENT 1

Immobilization of DNA on a Glass Surface as a Function of Time and Probe Concentration 75 mm×25 mm×0.96–1.6 mm thick glass microscope slides (Corning or Clay Adams) were cleaned by incubating them in 1M $HNO_3$ for 30–40 minutes. After incubation, slides were washed twice with water and then sonicated successively in hexane, acetone and ethanol (10 minutes per sonication). After washing, slides were dried at 85° C. for two hours.

1,3-phenylene diisocyanate was dissolved in toluene to a final concentration of 1.5% and imidazole was then added. The final solution had 2 moles of imidazole for each mole of isocyanate. The solution was sonicated for 2 minutes and then applied to the washed glass slides. Incubation proceeded at room temperature overnight. After incubation, slides were washed sequentially with toluene and acetone and then dried at room temperature for 5–10 minutes. The slides were kept in a vacuum desiccator until reactions for the attachment of probes were performed.

The slides, containing surface-bound reactive groups, were reacted with $^{32}P$ amino-derivatized oligonucleotides at room temperature for varying periods of time. Probes were reacted at concentrations of 10 μM, 20 μM, 50 μM and 100 μM. In separate reactions, the identical experiment was carried out using non-amino derivatized probes. After probe attachment, slides were washed with water (15 minutes); 30% ammonia (1 hour); and again with water. The slides were then dried and the amount of radioactivity retained under each reaction condition was determined using a phosphorimager. The total amount of probe available for attachment under each condition was determined by applying labelled oligonucleotides to slides but not washing prior to determining the amount of radioactivity present. The number of PSLs present on unwashed slides was divided into the PSLs obtained under each reaction condition and multiplied by 100 to determine percentages. Results are shown in Tables 5 and 6.

TABLE 5

IMMOBILIZATION OF AMINO-DERIVATIZED PROBES ON GLASS AS A FUNCTION OF TIME

| Oligonucleotide Concentration | Incubation Time (min.) | Percent of Total Oligonucleotide Bound | pmoles Bound |
|---|---|---|---|
| 10 μM | 0 | 0.84 | 0.025 |
| | 5 | 0.68 | 0.020 |
| | 15 | 0.88 | 0.026 |
| | 30 | 1.24 | 0.037 |
| | 60 | 1.54 | 0.046 |
| | 90 | 1.12 | 0.034 |
| | 120 | 0.91 | 0.027 |
| 20 μM | 0 | 0.33 | 0.020 |
| | 5 | 0.5 | 0.030 |

TABLE 5-continued

IMMOBILIZATION OF AMINO-DERIVATIZED PROBES
ON GLASS AS A FUNCTION OF TIME

| Oligonucleotide Concentration | Incubation Time (min.) | Percent of Total Oligonucleotide Bound | pmoles Bound |
|---|---|---|---|
| | 15 | 0.51 | 0.031 |
| | 30 | 1.01 | 0.061 |
| | 60 | 0.81 | 0.049 |
| | 90 | 0.40 | 0.024 |
| | 120 | 0.52 | 0.031 |
| 50 μM | 0 | 0.30 | 0.009 |
| | 5 | 0.60 | 0.018 |
| | 15 | 0.64 | 0.019 |
| | 30 | 0.94 | 0.028 |
| | 60 | 0.76 | 0.023 |
| | 90 | 0.64 | 0.019 |
| | 120 | 0.47 | 0.014 |
| 100 μM | 0 | 0.13 | 0.039 |
| | 5 | 0.22 | 0.066 |
| | 15 | 0.41 | 0.123 |
| | 30 | 0.59 | 0.177 |
| | 60 | 0.63 | 0.189 |
| | 90 | 0.25 | 0.075 |
| | 120 | 0.39 | 0.117 |

TABLE 6

IMMOBILIZATION OF NON-AMINO PROBES ON
GLASS AS A FUNCTION OF TIME

| Probe Concentration | Incubation Time (min.) | Percent of Total Probe Attached | pmoles Bound |
|---|---|---|---|
| 10 μM | 0 | 0.43 | 0.013 |
| | 5 | 0.55 | 0.017 |
| | 15 | 0.55 | 0.017 |
| | 30 | 0.58 | 0.017 |
| | 60 | 0.51 | 0.015 |
| | 90 | 0.65 | 0.013 |
| | 120 | 0.58 | 0.017 |
| 20 μM | 0 | 0.34 | 0.020 |
| | 5 | 0.49 | 0.029 |
| | 15 | 0.58 | 0.035 |
| | 30 | 0.46 | 0.028 |
| | 60 | 0.46 | 0.028 |
| | 90 | 0.46 | 0.028 |
| | 120 | 0.40 | 0.024 |
| 50 μM | 0 | 0.30 | 0.045 |
| | 5 | 0.45 | 0.068 |
| | 15 | 0.62 | 0.093 |
| | 30 | 0.43 | 0.065 |
| | 60 | 0.67 | 0.101 |
| | 90 | 0.75 | 0.113 |
| | 120 | 0.52 | 0.078 |
| 100 μM | 0 | 0.31 | 0.093 |
| | 5 | 0.31 | 0.096 |
| | 15 | 0.42 | 0.126 |
| | 30 | 0.60 | 0.180 |
| | 60 | 0.45 | 0.135 |
| | 90 | 0.50 | 0.150 |
| | 120 | 0.58 | 0.174 |

The results indicate that the attachment of probe is essentially complete by 30 minutes after the reaction has begun. Substantial binding occurred at all of the concentrations of oligonucleotide examined.

EXPERIMENT 2

Hybridization of Immobilized Oligonucleotide Probes to Labelled Target Sequences, Effect of Dimethyl Sulfoxide Glass slides were washed as described above and then reacted with phenylene isocyanate/imidazole dissolved in one of two solvents. On one set of slides (the "A" slides), toluene was used as the solvent for dissolving 1,3-phenylene diisocyanate and imidazole. On a second set (the "B" slides), 1,3-phenylene diisocyanate and imidazole were dissolved in tetrahydrofuran. The slides were sequentially washed with toluene and acetone and then stored dry until the time of probe attachment.

Amino-derivatized and non-derivatized oligonucleotide probes were reacted with the immobilized reactive groups bound to the surface of the slides. Reactions were performed using oligonucleotides at a concentration of 10 μM and proceeded for 15 minutes at room temperature; for 15 minutes at 37° C.; or for 2 hours at 37° C. After reaction, slides were washed in water (15 minutes); 30% ammonia (1 hour); and again in water (1 hour).

Figure 8:
FIG. 8. Glass slides were prepared using either 1,3-phenylene diisocyanate and imidazole dissolved in toluene (slides labelled as "A") or with 1.3-phenylene diisocyanate and imidazole dissolved in tetrahydrofuran (slides labelled as "B"). Slides were then reacted with either lightly labelled aminoderivatized oligonucleotide probes or lightly labelled non-derivatized oligonucleotide probes. Probes were reacted at room temperature for 15 minutes; at 37° C. for 15 minutes; or at 37° C. for two hours. After probe reactions were complete, hybridizations were performed between immobilized probes and more heavily labelled target DNAs with complementary nucleotide sequences. After hybridization, slides were washed with buffer and then exposed to a phosphor imager plate (Fuji) for a period of two minutes. Results are shown in the figure. The dark spots at the bottom of the figure were obtained by spotting slides with labelled target DNAs and then exposing the slides to a phosphorimager plate for 2 minutes (i.e., slides were not washed prior to exposure). These results represent the total exposure that could be obtained if all target sequences completely hybridized to immobilized probes.
Figure 8:
Figure 8:
Figure 9:
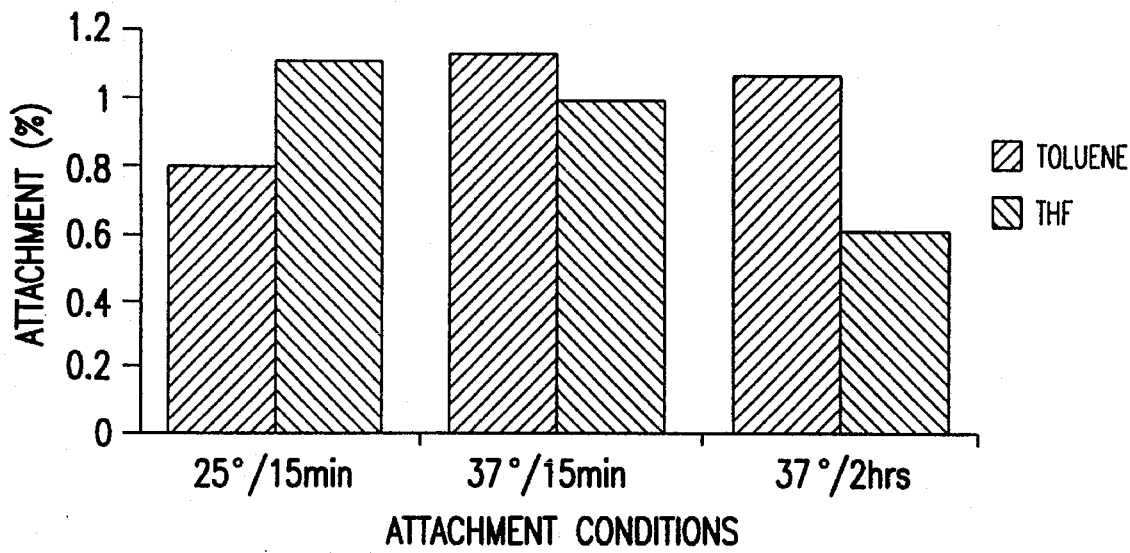
FIG. 9. Glass slides were prepared using 1,3-phenylene diisocyanate and imidizole in toluene and tetrahyrdofuran (THF). The amount of probe attached under each condition is expressed as a percentage of the total probe applied.

The immobilized probes, which were lightly labelled with $^{32}P$, were then hybridized with much more heavily labelled target oligonucleotides having complementary nucleotide sequences. Hybridization proceeded at 6° C. overnight. At the end of this time, slides were washed with hybridization solution for 1.5 hours at room temperature, dried, and then exposed to a phosphor imaging plate for a period of 2 minutes. Results are shown in FIGS. 8 and 9.

It can be seen from the figure that strong hybridization occurred to spots containing the amino-derivatized probes regardless of whether the probes had been attached at 37° C. for 2 hours, 37° C. for 15 minutes, or at room temperature for 15 minutes. No significant binding was observed at sites where non-amino probes were spotted. At the very bottom of FIG. 8, are the images that were obtained when slides were spotted with labelled target nucleotides but were not washed prior to exposure. The results indicate that toluene and tetrahydrofuran serve about equally well as solvents in the derivatization of glass plates with isocyanates.

Figure 10:
FIG. 10. Glass slides were prepared using 1,3-phenylene diisocyanate and imidazole dissolved in dimethyl sulfoxide (DMSO). Amino-derivatized or non-derivatized oligonucleotide probes were reacted at a concentration of 10 µM and the immobilized probes were hybridized to labelled target oligonucleotides containing complementary nucleotide sequences. After hybridization and washing, slides were exposed to a phophor imaging plate for a period of 30 minutes.
Figure 11:
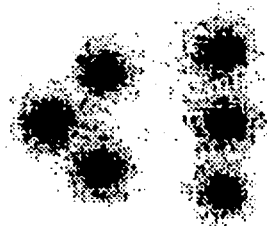
FIG. 11. The hybridization experiment described in FIG. 10 was repeated using either dry DMSO or commercial, unpurified DMSO and the results from a 10 minute exposure to phosphor imaging plate are shown in FIG. 11. The dark spots at the bottom of the figure (slide 1) represent images obtained by spotting labelled target oligonucleotide on an untreated slide. The three spots in a triangular pattern on the left side of slide 1 occur at positions where non-amino, labelled probes were reacted with the untreated slide. Non-amino probes were also reacted at approximately the same locations on slides 2 and 3 but little or no radioactivity remained at these positions after slides were washed, i.e., there is little or no image present after exposure to phosphor imager.

In a separate experiment, dimethyl sulfoxide was used as the solvent for 1,3-phenylene diisocyanate/imidazole. Oligonucleotide probes were attached at a concentration of 10 μM and the reaction proceeded for 30 minutes at room temperature. The immobilized probes were washed as described above and then hybridized to $^{32}P$-labelled target oligonucleotides having complementary nucleotide sequences. Incubation took place overnight at a temperature of 6° C. in the presence of tetramethyl ammonium chloride (TMAC). At the end of the incubation, plates were washed with hybridization buffer, dried, and then exposed to a phosphor imaging plate. The results shown in FIG. 10 indicate that the use of dimethyl sulfoxide as solvent produced a dramatic increase in the amount of hybridization. Similar results were obtained when the experiment was repeated using either dry DMSO or commercial (i.e., undistilled) DMSO (FIG. 11). Importantly, no significant hybridization was observed when these hybridization experiments were repeated using probes with nucleotide mismatches relative to target (mut 551 and mut 549). Again, no hybridization was observed at sites where non-amino probes were spored on the glass slides.

In order to determine the extent to which probe attachment to glass slides was facilitated by the use of DMSO, attachment was studied at room temperature as a function of time and probe concentration. These experiments were conducted in essentially the same way as the experiments whose results are shown in Tables 5 and 6 except that DMSO was present in probe attachment reactions. Results for the attachment of amino-derivatized probes are shown in Table 7 and results for non-derivatized probes, are shown in Table 8.

TABLE 7

IMMOBILIZATION OF AMINO-DERIVATIZED PROBES ON GLASS IN THE PRESENCE OF DMSO

| Oligonucleotide Concentration | Incubation Time (min.) | Percent of Total Oligonucleotide Bound | pmoles Bound |
|---|---|---|---|
| 10 μM | 5 | 3.49 | 0.105 |
|  | 15 | 3.35 | 0.101 |
|  | 30 | 3.24 | 0.097 |
|  | 60 | 8.04 | 0.241 |
|  | 90 | 6.06 | 0.182 |
|  | 120 | 9.04 | 0.271 |
| 20 μM | 5 | 1.01 | 0.061 |
|  | 15 | 2.96 | 0.178 |
|  | 30 | 2.64 | 0.158 |
|  | 60 | 9.76 | 0.586 |
|  | 90 | 9.66 | 0.580 |
|  | 120 | 9.78 | 0.587 |
| 50 μM | 5 | 3.30 | 0.495 |
|  | 15 | 2.48 | 0.372 |
|  | 30 | 2.62 | 0.393 |
|  | 60 | 2.73 | 0.409 |
|  | 90 | 4.74 | 0.711 |
|  | 120 | 2.87 | 0.431 |
| 100 μM | 5 | 4.02 | 1.206 |
|  | 15 | 4.08 | 1.224 |
|  | 30 | 7.67 | 2.301 |
|  | 60 | 7.31 | 2.193 |
|  | 90 | 8.43 | 2.529 |
|  | 120 | 8.40 | 2.520 |

TABLE 8

IMMOBILIZATION OF NON-AMINO PROBES ON GLASS IN THE PRESENCE OF DMSO

| Probe Concentration | Incubation Time (min.) | Percent of Total Probe Attached | pmoles Bound |
|---|---|---|---|
| 10 μM | 5 | 0.14 | 0.004 |
|  | 15 | 0.41 | 0.012 |
|  | 30 | 0.47 | 0.014 |
|  | 60 | 0.50 | 0.015 |
|  | 90 | 0.95 | 0.029 |
|  | 120 | 1.45 | 0.044 |
| 20 μM | 5 | 0.19 | 0.011 |
|  | 15 | 0.30 | 0.018 |
|  | 30 | 0.61 | 0.037 |
|  | 60 | 0.5 | 0.034 |
|  | 90 | 0.69 | 0.041 |
|  | 120 | 0.53 | 0.032 |
| 50 μM | 5 | 0.23 | 0.035 |
|  | 15 | 0.19 | 0.029 |
|  | 30 | 0.27 | 0.041 |
|  | 60 | 0.28 | 0.042 |
|  | 90 | 0.38 | 0.057 |
|  | 120 | 0.20 | 0.030 |
| 100 μM | 5 | 0.43 | 0.129 |
|  | 15 | 0.33 | 0.099 |
|  | 30 | 0.29 | 0.087 |
|  | 60 | 0.31 | 0.093 |
|  | 90 | 0.26 | 0.078 |
|  | 120 | 0.66 | 0.198 |

A comparison of the results shown in Tables 7 and 8 with those in Tables 5 and 6 indicates that DMSO improves the attachment of amino derivatized probes to glass by a factor of between 4 and 10 fold but has little, if any, effect on the attachment of non-derivatized probes.

C. CONCLUSIONS

The conclusions that can be drawn from the above experiments are that glass surfaces can be derivatized using isocyanates or isothiocyanates. The preferred procedure for derivatization includes incubation of the derivatizing agent and imidazole in a solvent of dimethyl sulfoxide. Oligonucleotide probes immobilized in this manner retain the ability to specifically hybridize to nucleic acids having complementary nucleotide sequences.

III. Immobilization of Nucleic Acids on a Surface of Aminated Polypropylene

A. Description of Immobilization Procedure

Figure 12:
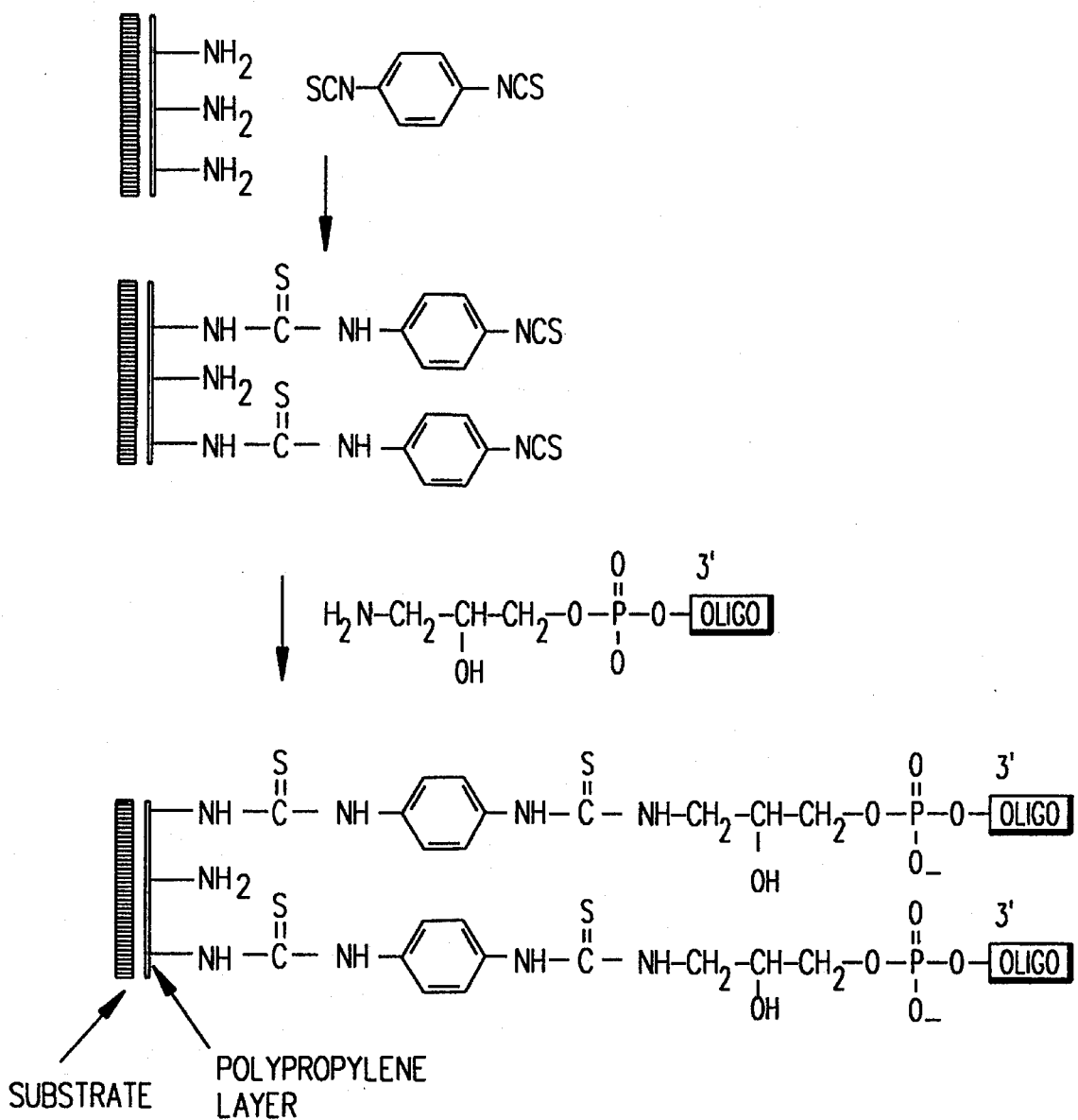
FIG. 12.

In addition to methods for immobilizing molecules on surfaces of platinum and glass, the present invention is directed to a procedure for immobilizing amino-derivatized oligonucleotides on a surface of aminated polypropylene. The general scheme for accomplishing such immobilization is shown in FIG. 12 using phenylene diisothiocyanate.

Preferably aminated polypropylene surfaces are incubated with derivatizing agent (either an isocyanate or an isothiocyanate) that has been dissolved in a solution of dimethyl formamide/pyridine. The solution is applied to the surface and then heated for about 2 to 2.5 hours at a temperature of about 55° C. After incubation, surfaces are washed (e.g., with dimethyl formamide and acetone) and then dried prior to attachment of oligonucleotide probes.

Amino-derivatized oligonucleotides react with surface bound groups to form covalent bonds. Reaction at room temperature for about 20 minutes has been found to produce good results. After washing in appropriate solutions (e.g., solutions of water and 30% ammonia), hybridizations may be performed to samples containing nucleic acids. The conditions of the hybridization reaction may be varied according to the desires of the experimenter (see e.g., Maskos et al., *Nucl. Acids Res.* 20:1679–1684 (1992); Southern et al., *Genomics* 13:1008–1017 (1992)). One procedure that has been found to work successfully is to incubate immobilized probes with $^{32}P$ labelled target DNAs in tetramethyl ammonium chloride (TMAC) overnight.

After washing surfaces to remove unbound target nucleic acids, hybridized molecules may be identified using well-established procedures. For example, target DNAs labelled with $^{32}P$ may be visualized using a phosphor imaging plate.

B. Example, Illustrating the Procedure

Unless otherwise noted, the following procedures were used in experiments concerned with the immobilization of nucleic acids on aminated polypropylene surfaces.

Modification of Surface

A solution for modifying the surface of aminated polypropylene is prepared by dissolving 30 mg of 1,4-phenylene diisothiocyanate in 1.8 ml of dry dimethyl formamide and then adding 0.2 ml pyridine. The solution is mixed well and then used to cover polypropylene films (1.5–2 cm square). The films are placed in a beaker which is covered with parafilm and then heated in a water bath at 55° C. for 2.5 hours. At the end of this time, the polypropylene film is removed and washed 4 times with dimethyl formamide and 3 times with acetone. The polypropylene is then dried at room temperature.

Probe Attachment

Oligonucleotide dissolved in water (300 nl) is applied to the surface of polypropylene films which have been fixed on filter paper or some other support (e.g., glass plates). The preparation is incubated at room temperature for approximately 20 minutes. At the end of this period, the polypropylene film is washed using the same procedure described above for glass slides.

Hybridization

The polypropylene film is fixed on a glass slide by applying tape at the film's four corners. Thereafter, the same hybridization procedures as those for platinum chips and glass slides are used for the polypropylene films. After hybridization is complete, the coverslip is removed from the polypropylene film which is then detached from the glass slide. The film is washed with precooled (6° C.) hybridization solution (without oligonucleotides or PEG) 4 or 5 times. The film is then air dried, wrapped in saran wrap, and exposed to a phoshor imaging plate. If desired, background radiation can be reduced by again washing the film in hybridization solution at 6° C. for 1 or 2 hours.

EXPERIMENT 1

Immobilization of Oligonucleotide Probes as a Function of Time and Concentration Aminated polypropylene supports (1.5 inches×1.5 inches) were obtained from Beckman Instruments (see, Matson et at., *Anal. Biochem.* 217:306–310 (1994)) and were incubated in a 1.5% solution of 1,4-phenylene diisothiocyanate dissolved in dimethyl formamide/pyridine (90:10). This solution was applied to the polypropylene surface, and incubated at about 55° C. for 2–2.5 hours. The polypropylene strips were washed with dimethyl formamide and acetone to remove unreacted 1,4-phenylene diisothiocyanate and then dried prior to the attachment of oligonucleotide probes.

$^3$P-labelled amino-derivatized oligonucleotides at concentrations of 10 μM, 20 μM, 50 μM and 100 μM were reacted with the isothiocyanate groups bound to the surface of the polypropylene. Reactions were carried out at room temperature for periods of time varying from 0 to 2 hours. Similar experiments were conducted using non-derivatized oligonucleotides. After incubation, plates were washed with water for 15 minutes; 30% ammonia for 1 hour; and water again for 15 minutes. The amount of radioactivity retained at each position on the surface was determined using a phosphorimager as described in sections I and II above. Results are shown in Tables 9 and 10.

TABLE 9

ATTACHMENT OF AMINO-DERIVATIZED OLIGO-
NUCLEOTIDES ON AMINATED POLYPROPYLENE AS A
FUNCTION OF TIME AND CONCENTRATION

| Oligonucleotide Concentration | Time (min.) | Percentage of Oligonucleotide Bound | pmoles Bound |
|---|---|---|---|
| 10 μM | 0 | 0.86 | 0.026 |
|  | 15 | 2.82 | 0.085 |
|  | 30 | 2.81 | 0.084 |
|  | 60 | 3.40 | 0.102 |
|  | 90 | 3.60 | 0.108 |
| 20 μM | 0 | 2.14 | 0.124 |
|  | 15 | 3.82 | 0.229 |
|  | 30 | 4.43 | 0.265 |
|  | 60 | 3.33 | 0.199 |
|  | 90 | 3.91 | 0.234 |
| 50 μM | 0 | 2.33 | 0.349 |
|  | 15 | 4.33 | 0.649 |
|  | 30 | 3.72 | 0.558 |
|  | 60 | 3.76 | 0.564 |
|  | 90 | 3.76 | 0.564 |
| 100 μM | 0 | 1.26 | 0.378 |
|  | 15 | 1.28 | 0.384 |
|  | 30 | 1.14 | 0.342 |
|  | 60 | 1.20 | 0.360 |
|  | 90 | 1.07 | 0.321 |

TABLE 10

ATTACHMENT OF NON-AMINO OLIGONUCLEOTIDES
ON AMINATED POLYPROPYLENE AS A FUNCTION
OF TIME AND CONCENTRATION

| Oligonucleotide Concentration | Time (min.) | Percentage of Oligonucleotide Bound | pmoles Bound |
|---|---|---|---|
| 10 μM | 0 | 0.34 | 0.010 |
|  | 15 | 0.35 | 0.011 |
|  | 30 | 0.35 | 0.011 |
|  | 60 | 0.48 | 0.014 |
|  | 90 | 0.41 | 0.012 |
| 20 μM | 0 | 0.46 | 0.028 |
|  | 15 | 0.56 | 0.034 |
|  | 30 | 0.82 | 0.049 |
|  | 60 | 0.67 | 0.040 |
|  | 90 | 0.64 | 0.038 |
| 50 μM | 0 | 0.57 | 0.086 |
|  | 15 | 0.86 | 0.130 |
|  | 30 | 0.96 | 0.144 |
|  | 60 | 0.94 | 0.141 |
|  | 90 | 0.89 | 0.134 |
| 100 μM | 0 | 0.87 | 0.261 |
|  | 15 | 1.59 | 0.477 |
|  | 30 | 1.42 | 0.426 |
|  | 60 | 1.22 | 0.366 |
|  | 90 | 1.12 | 0.336 |

The percentages shown in the above tables were determined based upon the total amount of oligonucleotide applied. This was determined by applying labelled oligonucleotides to a surface and determining the number of photostimulable light units using a phosphorimager without first washing the surface. The number of PSLs obtained under each hybridization condition was then determined, divided by the total available and multiplied by 100 to obtain the percentages shown.

The results indicate that, at zero time, there is essentially no difference between the results for the amino-derivatized probes and non-derivatized probes. Thereafter, the percentage of bound probes decreased for the non-derivatized oligonucleotides and increases for the amino-derivatized oligonucleotides. Reactions are essentially complete after about 15 minutes at room temperature. The attachment of amino-derivatized probes increased significantly in the time interval between 90 and 120 minutes, however, a substantial increase in the attachment of non-derivatized probes also occurred during this interval (probably due to interactions between surface-bound isothiocyanates and ring nitrogens on nucleobases in oligonucleotides).

Experiment 2

Hybridization of Target Oligonucleotides to Probes Immobilized on Aminated Polypropylene Surfaces Aminated polypropylene was derivatized with phenylene diisothiocyanate as described above and unlabelled, amino-derivatized oligonucleotide probes were attached. Attachment proceeded at room temperature for a period of 20 minutes using a probe concentration of 10 μM. Surfaces were washed in water for 15 minutes, 30% ammonia for 1 hour and again in water for 15 minutes.

$^{32}$P-labelled target oligonucleotides were hybridized to the immobilized probes using two slightly different procedures. In some experiments, target DNA was applied as a spot to surface positions where probes had been immobilized. In other experiments, a solution containing target DNA was used to coat the entire surface by covering the surface with a cover slip.

In order to determine whether hybridization was occurring specifically to target DNAs having complementary nucleotide sequences, two different types of oligonucleotides were used as probes. In certain positions on the polypropylene surface, probes were attached that had nucleotide sequences exactly complementary to targets. At other positions, probes were attached which contained a one nucleotide mismatch.

Hybridization was performed at 6° C. overnight. After incubation, polypropylene surfaces were washed in hybridization buffer at room temperature with a pipette. In other experiments, it was found that better results could be obtained when washing took place at 6° C. The surfaces were then exposed to a phosphor imaging plate and results are shown in FIG. 13.

The positions on the film designated as "WT probes" are positions where wild type probes were attached (i.e., probes with sequences exactly complementary to the sequence of the target oligonucleotides). The positions marked as "MM probes" are positions where probes containing mismatched sequences were immobilized. It can be seen that the wild type probes produced a strong hybridization signal whereas the mismatched probes produced little or no signal. This is an indication that the probes immobilized using the procedures described above retain their ability to specifically recognize and bind oligonucleotides with complementary nucleotide sequences.

Figure 13:
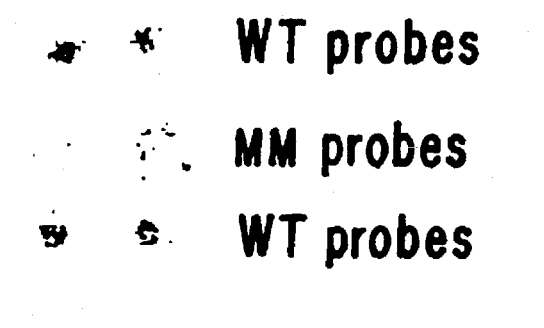

FIG. 13 shows the results that were obtained when target oligonucleotides were spotted at positions of probe immobilization. When the experiment was performed using the cover slip method, similar results were obtained. This is an indication that non-specific adsorption to the polypropylene surface is not a major problem.

Figure 14A:
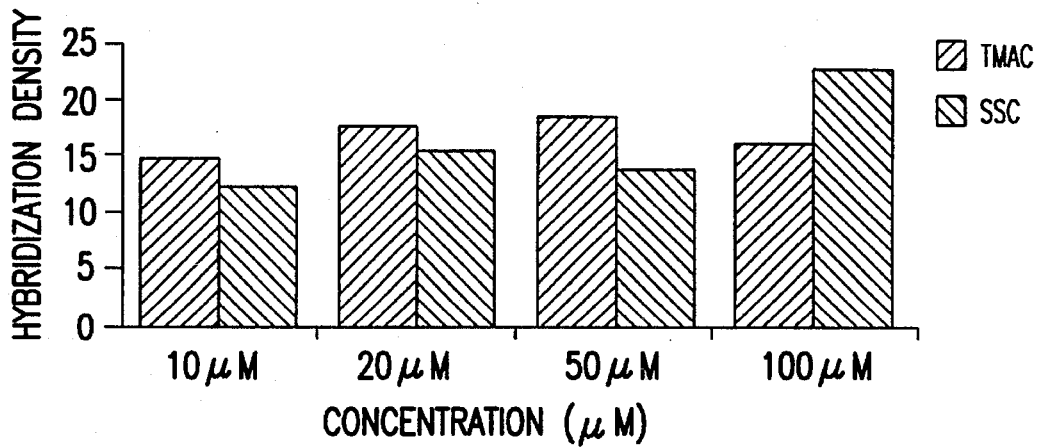
FIG. 14 (panel A)–FIG. 14 (panel B).
Figure 14B:
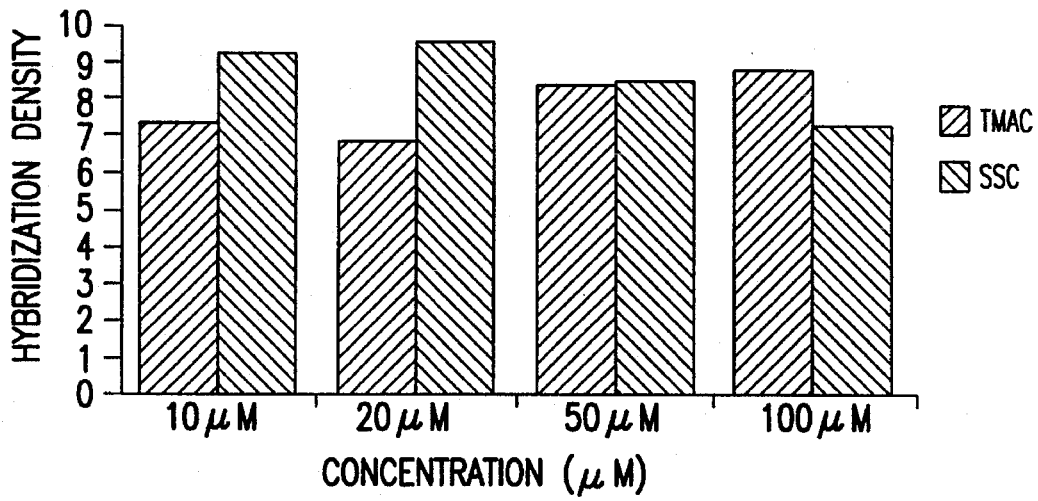

In a separate experiment, wild type probes were attached at concentrations of 10 μM, 20 μM, 50 μM and 100 μM. Attachment took place at room temperature for a period of 20 minutes. Hybridization with $^{32}$P labelled target DNA was performed at 6° C., overnight, in a hybridization solution containing either tetramethyl ammonium chloride (TMAC) or saline sodium citrate (SSC). After hybridization, polypropylene films were washed in water and 30% ammonia, dried and exposed to a phosphor imaging plate. As can be seen in the results shown in FIGS. 14A and 14B, significant hybridization occurred when probes were immobilized at any of the concentrations examined.

C. CONCLUSIONS

It can be concluded from the above results that aminated polypropylene can be derivatized with isothiocyanate and used for immobilizing amino-derivatized oligonucleotides. These immobilized oligonucleotides retain their ability to specifically hybridize to complementary sequences and can distinguish between wild type target oligonucleotides and target oligonucleotides containing mismatches. It appears that probes may be immobilized on polypropylene surfaces at concentrations from 10 to 100 μM without destroying their ability to effectively hybridize to target.

V. Utility of Immobilized Molecules

Solid supports with surfaces containing immobilized molecules may be used for a wide variety of different purposes. For example, such supports have been used in biochemical separations (U.S. Pat. No. 5,153,166, issued 1992) and in immunoassays (U.S. Pat. No. 5,314,830, issued 1994).

Immobilized enzymes often retain the ability to catalyze chemical reactions (see e.g. Akashi et at., *Bioconjugate Chem.* 3:363-365 (1992)) and can be easily separated from reaction products. As a result, enzymes immobilized on solid supports provide a convenient tool for use in research or for the commercial production of foods, beverages or chemicals.

In the area of molecular biology, both peptides and oligonucleotides may be immobilized on solid or semi-solid supports during synthesis (U.S. Pat. No. 5,143,854) and immobilized nucleic acids have long been used in carrying out different types of hybridizations (see e.g., Southern et al., *Genomics* 13:1008-1017 (1992) Maniatis, T., et al., *Molecular Cloning, A Laboratory Manual*, Cold Spring Harbor Laboratories. Cold Spring Harbor, N.Y. (1982)); and Hames, B. D., et al., *Nucleic Acid Hybridization, Practical Approach*, IRL Press, Washington, D.C. (1985)). Recent studies have suggested that nucleic acids immobilized on a variety of supports may provide a means for automated DNA sequence analysis and for the rapid analysis of biological samples (Beattie: et al., *Clin. Chem.* 39:719-722 (1993); Drmanac et al., *Science* 260:1649-1652 (1993); Saiki, et al., *Proc. Natl. Acad. Sci. USA* 86:6230-6234 (1989)).

All references cited above are fully incorporated by reference. Having now fully described the invention, it will be understood by those of skill in the art that the invention may be performed within a wide and equivalent range of conditions, parameters and the like, without affecting the spirit or scope of the invention or any embodiment thereof. It will also be understood that the specific examples which are provided herein are for the purposes of illustration only and are not intended to be limiting unless otherwise specified.

What is claimed is:

1. A method for immobilizing an amino-containing molecule on a platinum surface, comprising the steps of:

(a) reacting said platinum surface with an isocyanate or an isothiocyanate to produce immobilized reactive moieties; and (b) reacting said immobilized reactive moieties with said molecule.

2. The method of claim 1, wherein said platinum surface is reacted with an isothiocyanate.

3. The method of claim 2, wherein said isothiocyanate is 1,4-phenylene diisothiocyanate.

4. A device comprising a platinum surface with immobilized molecules, wherein said surface is prepared by the method of claim 1.

5. A method for immobilizing a nucleic acid on a platinum surface, comprising the steps of:

a) reacting said platinum surface with an isocyanate or an isothiocyanate to produce immobilized reactive moieties; and (b) reacting said immobilized reactive moieties with a nucleic acid derivatized to contain an amino group.

6. The method of claim 5, wherein said surface is reacted with an isothiocyanate.

7. The method of claim 6, wherein said isothiocyanate is a diisothiocyanate.

8. The method of claim 7, wherein said diisothiocyanate is 1,4-phenylene diisothiocyanate.

9. The method of claim 5, wherein said oligonucleotide is present at a concentration of between 10 and 20 μM and the incubation of step b) proceeds for about 15-20 minutes at room temperature, about 25° C.

10. A device comprising a platinum surface with an immobilized nucleic acid, wherein said surface is prepared by the method of claim 5.

* * * * *